US007166638B2

(12) United States Patent
Benedini et al.

(10) Patent No.: US 7,166,638 B2
(45) Date of Patent: Jan. 23, 2007

(54) STATIN DERIVATIVES

(75) Inventors: Francesca Benedini, Milan (IT); Ennio Ongini, Segrate (IT); Piero Del Soldato, Monza (IT)

(73) Assignee: Nicox S.A., Spohia Anitpolis (FR)

( * ) Notice: Subject to any disclaimer, the term of this patent is extended or adjusted under 35 U.S.C. 154(b) by 0 days.

(21) Appl. No.: 10/849,561

(22) Filed: May 20, 2004
(Under 37 CFR 1.47)

(65) Prior Publication Data
US 2005/0165084 A1    Jul. 28, 2005

(30) Foreign Application Priority Data
May 27, 2003    (EP)    ................... 03101530

(51) Int. Cl.
A61K 31/40    (2006.01)
A61K 31/401   (2006.01)
C07D 209/10   (2006.01)
C07D 207/325  (2006.01)

(52) U.S. Cl. .................. 514/423; 514/509; 514/419; 548/507; 548/537

(58) Field of Classification Search ............... 514/423; 548/537
See application file for complete search history.

(56) References Cited

U.S. PATENT DOCUMENTS 6,476,235 B1 *    11/2002    Butler et al. ................. 548/517

FOREIGN PATENT DOCUMENTS

| WO | 97/16405       | 5/1997  | ..................... 203/4 |
| WO | WO 97/16405    | 5/1997  |                              |
| WO | 98/21193       | 5/1998  | .................. 285/10   |
| WO | WO 00/61537    | 10/2000 |                              |
| WO | WO 00/61541    | 10/2000 |                              |
| WO | WO 01/12584 A2 | 2/2001  |                              |
| WO | WO 03/007846 A1| 1/2003  |                              |

OTHER PUBLICATIONS

Carini, et al., "In Vitro Metabolism of a nitroderivative of acetyl-salicylic acid (NCX4016) by rat liver: LC and LC-MS studies," J. Phar. Biomed. Anal. 29 (2002) 1061-71.*
Chiroli, et al. "Nitric oxide-donating non-steroidal anti-inflammatory drugs: the case of nitorderivatives of asprin," European J. Med. Chem. 38 (2003) 441-446. (available online Mar. 26, 2003).*
Baraldi, et al. "Synthesis of Nitro Esters of PRedisolone, New Compounds Combining Pharmacological Properties of Both Glucocorticoids and Niitric Oxide," J. Med. Chem. 2004, vol. 47, 711-719.*
Burgaud, et al., Nitric Oxide-Releasing Drugs A Novel Class of Efective and Safe Therapeutic Agents, Ann. N.Y. Acad. Sci. 962: 360-371 (2002).*
Hobbs, et al. "Achievement of English National Service Framework Lipid-lowering Goals: Pooled Data from Recent Comparative Treatment Trials of Statins at Starting Doses" J. Clin. Pract., vol. 59, 10 (2005), 1171-1177.*
Omori, et al. "Direct in vivo evidence of a vascular statin: a single dose of cerivastatin rapidly increases vascular endothelial responsiveness in healthy normocholesterolaemic subjects," British J. Clin. Pharmacol., vol. 54, 395, 399 (2002).*
Shishehbor, et al., "Statins Promote Potent Systemic Antioxidant Effects Through Specific Inflammatory Pathways" Circulation. 2003; 108: 426-431.*
Laufs, et al. "Atorvastatin Upregulates Type III Nitric Oxide Synthase in Thombocytes, Decreases Platelet Activation, and Protects From Cerebral Ischemia in Normocholesterolemic Mice Editorial Comment" Stroke, 2000: 32: 2442-2449.*
Semeraro et al., "Direct Induction of Tissue Factor Synthesis by Endotoxin In Human Macrophages From Diverse Anatomical Sites," *Immunology* 50 529-535, 1983.
Vezza et al., "Prostaglandin $E_2$ Potentiates Platelet Aggregation by Priming Protein Kinase C," *Blood* 82 2704-2713, 1993.
Rossiello et al., "Fibrin Down-regulates LPS- and PMA-induced Tissue Factor Expression by Blood Momonuclear Cells," *Thromb Haemost* 84 453-459, 2000.
Momi et al., "Prevention of Pulmonary Thromboembolism by NCX 4016, a Nitric Oxide-Releasing Asprin," *European Journal of Pharmacology* 397 177-185, 2000.
Emanueli et al., "Local Delivery of Human Tissue Kallikrein Gene Accelerates Spontaneous Angiogenesis in Mouse Model of Hindlimb Ischemia," *Circulation* 2/9 125-132, 2001.
Wanstall et al al., "Vascular Smooth Muscle Relaxation Mediated by Nitric Oxide Donors: A Comparison with Acetylcholine, Nitric Oxide and Nitroxyl Ion," *British Journal of Pharmacology* 134 463-472, 2001.
Bonetti et al., "Statin Effects Beyond Lipid Lowering—Are They Clinically Relevant?," *European Heart Journal* 24 225-248, 2003.
Ongini et al., Nitric Oxide (NO)-Releasing Statin Derivatives, A Class of Drugs Showing Enhanced Antoproliferative And Antiinflammatory Properties, *PNAS* 101 8497-8502, 2004.
Bonazzi et al., "New Nitric Oxide (NO)-releasing Statin Derivatives With Enhanced Anti-Inflammatory Properties," *AHA Scientific Sessions* 9-12, 2003.
Dever et al., "Effects of No-Pravastatin on Leukocyte Adhesion and Reactive Oxygen Species Generation in Control and Apoe Knockout Mice," *AHA Scientific Sessions* 9-12, 2003.
Rossiello et al., "Nitropravastatin (NCX6550) Exerts an Antiplatelet/ Antithrombotic Activity and Inhabits Tissue Factor Expression," *AHA Scientific Sessions* 9-12, 2003.
Emanueli et al., "The Nitric Oxide (NO)-Releasing Pravastatin Derivative, NCX 6550, Potentiates Reparative Angiogenesis In A Mouse Model Of Peripheral Ischemia," *BPS*, 2003.
Guzzetta et al., "Nitric Oxide (NO)-Releasing Statins: A New Class of Drugs Combining NO and Statin Properties," *BPS*, 2003.
Momi et al., "Antiplatelet and Antithrombotic Activity of NCX 6550, A Nitrick Oxide (NO)-Releasing Derivative of Pravastatin," *BPS*, 2003.
Guzzetta et al., "Novel Nitric Oxide (NO)-releasing Derivatives of Statins Modulate Cellular NO Homeostasis Acting on eNOS and iNOS Expressions," 9th*International Conference on Alzheimer's Disease and Related Disorders*, 2004.

* cited by examiner

Primary Examiner—Joseph K. McKane
Assistant Examiner—Nyeemah Grazier
(74) Attorney, Agent, or Firm—Arent Fox PLLC

(57) ABSTRACT

Statin nitroderivatives having improved pharmacological activity and enhanced tolerability are described. They can be employed for treating and/or preventing several diseases, in particular coronary syndromes, neurodegenerative disorders as well as for reducing cholesterol levels.

21 Claims, No Drawings

STATIN DERIVATIVES

The present invention relates to new statin derivatives. More particularly, the present invention relates to statin nitroderivatives, pharmaceutical compositions containing them and their use as cholesterol-reducing drugs, as drugs having immunosuppressive properties, antioxidant, anti-thrombotic and anti-inflammatory activity, effects on endothelial function, and for treating and/or preventing acute coronary syndromes, stroke, neurodegenerative disorders, such as Alzheimer's and Parkinson's disease as well as autoimmune diseases, such as multiple sclerosis.

With statins a class of compounds is intended, comprising as main components lovastatin, simvastatin, pravastatin, mevastatin, fluvastatin, atorvastatin, rosuvastatin and cerivastatin (rivastatin). They possess a side group that is structurally similar to HMG-CoA (3-hydroxy-3-methylglutaryl coenzyme A). Fluvastatin, atorvastatin, rosuvastatin and cerivastatin are entirely synthetic compounds containing a heptanoic acid side chain, the remainders being fungal metabolites.

It is known that the various statins are inhibitors of HMG-CoA reductase, an enzyme which catalyses an early, rate-limiting step in cholesterol biosynthesis, reduce triglyceride levels and are also indicated for raising HDL-C levels (P. O. Bonetti et al., European Heart Journal (2003) 24, 225–248).

However, it is also known that statins exhibit adverse effects, such as for example hepatopathy, possible carcinogenic potential, muscular side-effects and, above all, myopathy.

It was now object of the present invention to provide new derivatives of statins able not only to eliminate or at least reduce the side effects associated with these compounds, but also having an improved pharmacological activity. It has been so surprisingly found that statin nitroderivatives have a significantly improved overall profile as compared to native statins both in term of wider pharmacological activity and enhanced tolerability. In particular, it has been recognized that the statin nitroderivatives of the present invention exhibit a strong anti-inflammatory, antithrombotic and anti-platelet activity and can be furthermore employed for reducing cholesterol and triglycerides levels, for raising HDL-C levels and for treating or preventing acute coronary syndromes, stroke, peripheral vascular diseases such as peripheral ischemia and all disorders associated with endothelial dysfunctions such as vascular complications in diabetic patients and atherosclerosis. They should also be employed for treating neurodegenerative and autoimmune diseases, such as Alzheimer's and Parkinson's disease as well as multiple sclerosis.

Object of the present invention are, therefore, statin nitroderivatives of general formula (I) and pharmaceutically acceptable salts or stereoisomers thereof

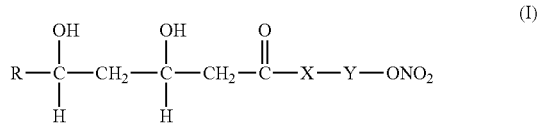

(I)

wherein R is the statin residue exemplified below and Y is a suitable linker group, X being as defined below.

According to the present invention, the statin residue R in formula (I) is selected from the group consisting of pravastatin, fluvastatin, cerivastatin, rosuvastatin and atorvastatin.

In particular, in the general formula (I) R, X and Y have the following meanings:

X is —O—, —S—, —NH— or —NHR$^1$—, R$^1$ being straight or branched alkyl with 1 to 10 carbon atoms, preferably CH$_3$;

R is

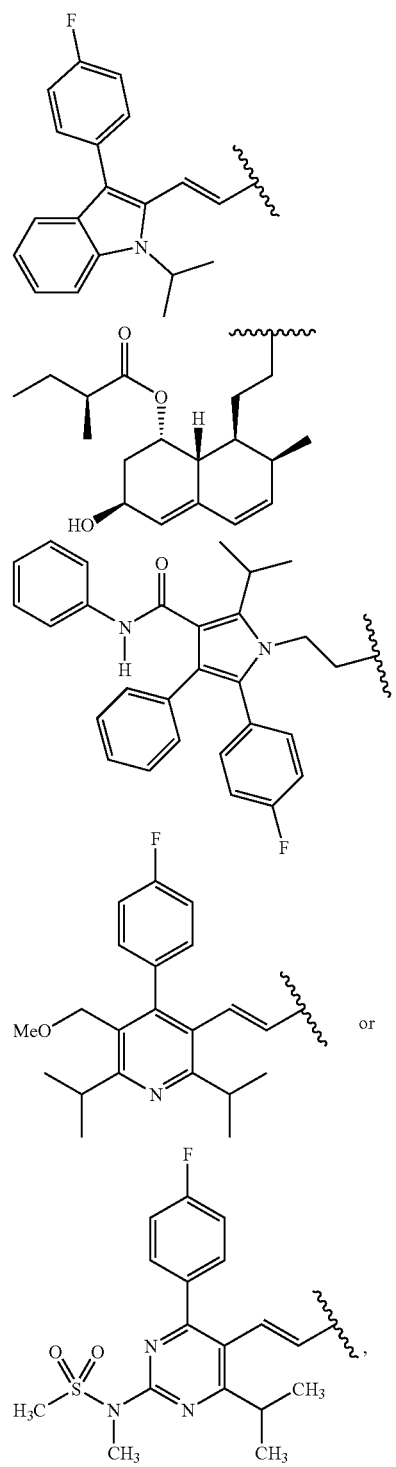

Y is a bivalent radical having the following meaning:
a)
straight or branched C$_1$–C$_{20}$ alkylene, preferably C$_1$–C$_{10}$, being optionally substituted with one or more of the substituents selected from the group consisting of: halogen atoms, hydroxy, —ONO$_2$ or T$_0$, wherein T$_0$ is —OC(O)(C$_1$–C$_{10}$ alkyl)-ONO$_2$ or —O(C$_1$–C$_{10}$ alkyl)-ONO$_2$;

cycloalkylene with 5 to 7 carbon atoms into cycloalkylene ring, the ring being eventually substituted with side chains T, wherein T is straight or branched alkyl with from 1 to 10 carbon atoms, preferably CH$_3$;

b)

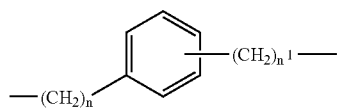

c)

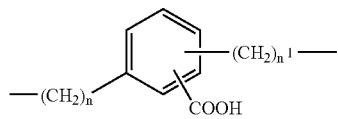

wherein n is an integer from 0 to 20, and n$^1$ is an integer from 1 to 20;

d)

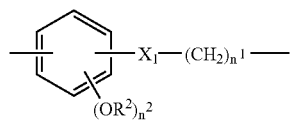

wherein:
n$^1$ is as defined above and n$^2$ is an integer from 0 to 2;
X$_1$=—OCO— or —COO— and R$^2$ is H or CH$_3$;

e)

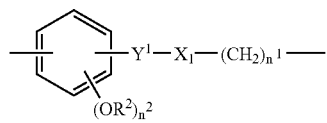

wherein:
n$^1$, n$^2$, R$^2$ and X$_1$ are as defined above;
Y$^1$ is —CH$_2$—CH$_2$— or —CH=CH—(CH$_2$)$_{n^2}$—;

f)

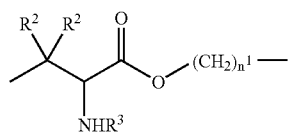

wherein:
n$^1$ and R$^2$ are as defined above, R$^3$ is H or COCH$_3$;
with the proviso that when Y is selected from the bivalent radicals mentioned under b)-f), the —ONO$_2$ group is bound to —(CH$_2$)$_n^1$;

g)

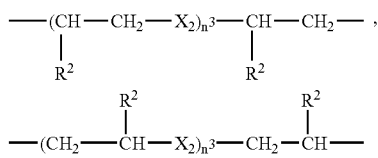

wherein X$_2$ is —O— or —S—, n$^3$ is an integer from 1 to 6, preferably from 1 to 4, R$^2$ is as defined above;

h)

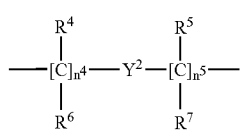

wherein:
n$^4$ is an integer from 0 to 10;
n$^5$ is an integer from 1 to 10;
R$^4$, R$^5$, R$^6$, R$^7$ are the same or different, and are H or straight or branched C$_1$–C$_4$-alkyl, preferably R$^4$, R$^5$, R$^6$, R$^7$ are H;
wherein the —ONO$_2$ group is linked to

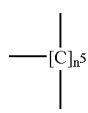

wherein n$^5$ is as defined above;
Y$^2$ is an heterocyclic saturated, unsaturated or aromatic 5 or 6 members ring, containing one or more heteroatoms selected from nitrogen, oxygen, sulfur, and is selected from

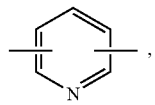 (Y1)

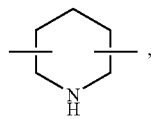 (Y2)

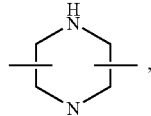 (Y3)

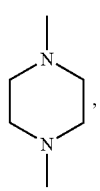 (Y4)

(Y5)

(Y6)

(Y7)

(Y8)

(Y9)

(Y10)

(Y11)

(Y12)

(Y13)

The term "$C_1$–$C_{20}$ alkylene" as used herein refers to branched or straight chain $C_1$–$C_{20}$ hydrocarbon, preferably having from 1 to 10 carbon atoms such as methylene, ethylene, propylene, isopropylene, n-butylene, pentylene, n-hexylene and the like.

The term "$C_1$–$C_{10}$ alkyl" as used herein refers to branched or straight chain alkyl groups comprising one to ten carbon atoms, including methyl, ethyl, n-propyl, isopropyl, n-butyl, isobutyl, t-butyl, pentyl, hexyl, octyl and the like.

The term "cycloalkylene" as used herein refers to ring having from 5 to 7 carbon atoms including, but not limited to, cyclopentylene, cyclohexylene optionally substituted with side chains such as straight or branched ($C_1$–$C_{10}$)-alkyl, preferably $CH_3$.

The term "heterocyclic" as used herein refers to saturated, unsaturated or aromatic 5 or 6 members ring, containing one or more heteroatoms selected from nitrogen, oxygen, sulphur, such as for example pyridine, pyrazine, pyrimidine, pyrrolidine, morpholine, imidazole and the like.

Another aspect of the present invention provides the use of the compounds of formula (I) in combination with at least a compound used to treat cardiovascular disease selected from the group consisting of: ACE inhibitors, angiotensin II receptor antagonists, beta-adrenergic blockers, calcium channel blockers, antithrombotics such as aspirin, nitrosated ACE inhibitors, nitrosated angiotensin II receptor antagonists, nitrosated beta-adrenergic blockers and nitrosated aspirin.

Suitable ACE inhibitors, angiotensin II receptor antagonists, beta-adrenergic blockers, calcium channel blockers, antithrombotics are described in the literature such as The Merck Index (13th edition).

Suitable nitrosated compounds are disclosed in WO 98/21193 and WO 97/16405.

The administration of the compounds above reported can be carried out simultaneously or successively.

The present invention also provides pharmaceutical kits comprising one or more containers filled with one or more of the compounds and/or compositions of the present invention and one or more of the compounds used to treat cardiovascular diseases reported above.

As stated above, the invention includes also the pharmaceutically acceptable salts of the compounds of formula (I) and stereoisomers thereof.

The compounds according to the present invention, when they contain in the molecule one salifiable nitrogen atom, can be transformed into the corresponding salts by reaction in an organic solvent such as acetonitrile, tetrahydrofuran with the corresponding organic or inorganic acids.

Examples of organic acids are: oxalic, tartaric, maleic, succinic, citric acids. Examples of inorganic acids are: nitric, hydrochloric, sulphuric, phosphoric acids. Salts with nitric acid are preferred.

The compounds of the invention which have one or more asymmetric carbon atoms can exist as optically pure enantiomers, pure diastereomers, enantiomers mixtures, diastereomers mixtures, enantiomer racemic mixtures, racemates or racemate mixtures. Within the object of the invention are also all the possible isomers, stereoisomers and their mixtures of the compounds of formula (I).

Preferred compounds are those of formula (I) wherein:
X is —O— or —S—;
R is a statin residue as defined above;
Y is a bivalent radical having the following meaning:

a) straight or branched $C_1$–$C_{10}$ alkylene, being optionally substituted with $T_0$, wherein $T_0$ is as above defined;

b)

—(CH$_2$)$_n$—⌬—(CH$_2$)$_{n^1}$— c)

—(CH$_2$)$_n$—⌬(COOH)—(CH$_2$)$_{n^1}$— wherein n is an integer from 0 to 5, and $n^1$ is an integer from 1 to 5;

d)

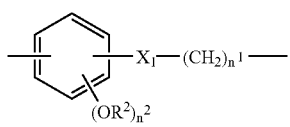

wherein:
$n^1$ is as defined above and $n^2$ is an integer from 0 to 2;
$X_1$=—OCO— or —COO— and $R^2$ is H or $CH_3$;

e)

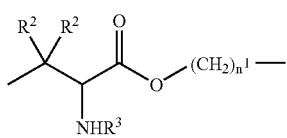

wherein:
$n^1$, $n^2$, $R^2$ and $X_1$ are as defined above;
$Y^1$ is —CH=CH—;

f)

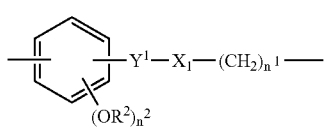

wherein:
$n^1$ is as defined above, $R^2$ is H or $CH_3$, $R^3$ is H or $COCH_3$;
with the proviso that when Y is selected from the bivalent radicals mentioned under b)-f), the —$ONO_2$ group is bound to —$(CH_2)_n^1$;

g)

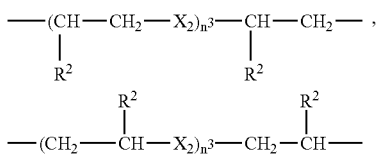

wherein $X_2$ is —O— or —S—, $n^3$ is an integer from 1 to 4, preferably 1, $R^2$ is a hydrogen atom or $CH_3$;

h)

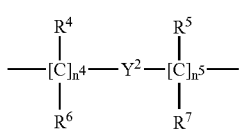

wherein:
$n^4$ is an integer from 0 to 3;
$n^5$ is an integer from 1 to 3;
$R^4$, $R^5$, $R^6$, $R^7$ are the same and are H;

and wherein the —$ONO_2$ group is linked to

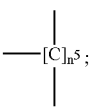

$Y^2$ is a 6 member saturated, unsaturated or aromatic heterocyclic ring, containing one or more atoms of nitrogen and selected for example from

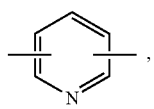 (Y5)

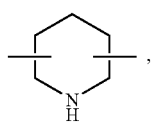 (Y13)

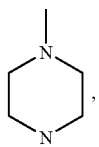 (Y1)

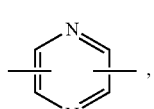 (Y2)

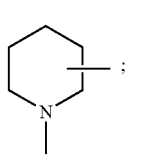 (Y4)

The following are preferred compounds according to the present invention:
fluvastatin 4-(nitrooxy)butyl ester,
fluvastatin 4-(nitrooxymetyl)benzyl ester,
fluvastatin 3-(nitrooxymethyl)benzyl ester,
fluvastatin 2-(nitrooxymethyl)benzyl ester,
fluvastatin 4-(nitrooxymethyl)phenyl ester,
fluvastatin 3-(nitrooxymethyl)phenyl ester,
fluvastatin 2-(nitrooxymethyl)phenyl ester,
fluvastatin 2-[2'-(nitrooxy)ethyloxy]ethyl ester, corresponding to formula:

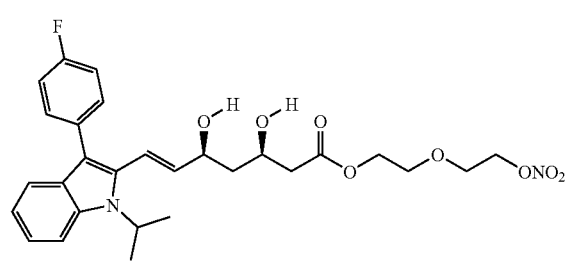

fluvastatin 2-methoxy-4-[[4'-(nitrooxy)butyl]trans-2-propenoyloxy]phenol ester, corresponding to formula:

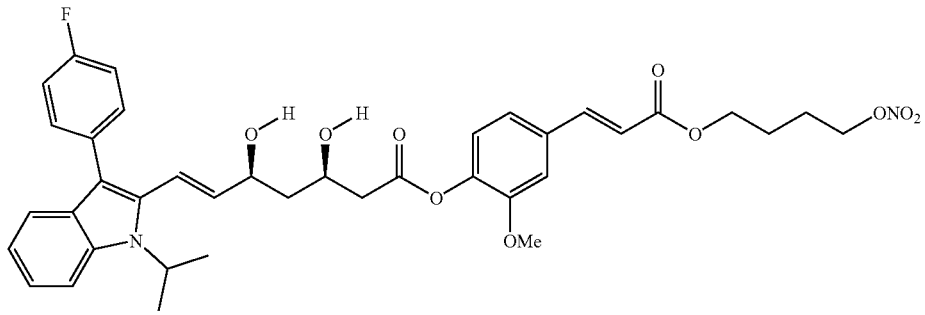

pravastatin 4-(nitrooxy)butyl ester,
pravastatin 4-(nitrooxymetyl)benzyl ester,
pravastatin 3-(nitrooxymethyl)benzyl ester,
pravastatin 2-(nitrooxymethyl)benzyl ester,
pravastatin 4-(nitrooxymethyl)phenyl ester,
pravastatin 3-(nitrooxymethyl)phenyl ester,
pravastatin 2-(nitrooxymethyl)phenyl ester,
pravastatin 2-[2'-(nitrooxy)ethyloxy]ethyl ester, corresponding to formula:

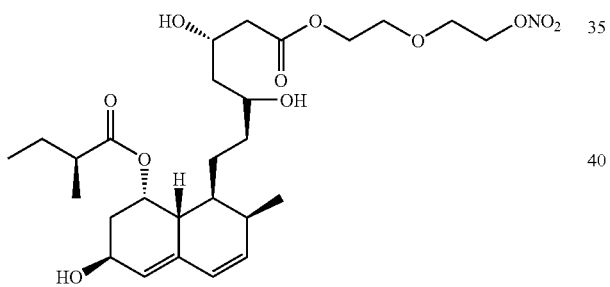

pravastatin 2-methoxy-4-[[4'-(nitrooxy)butyl]trans-2-propenoyloxy]phenol ester, corresponding to formula:

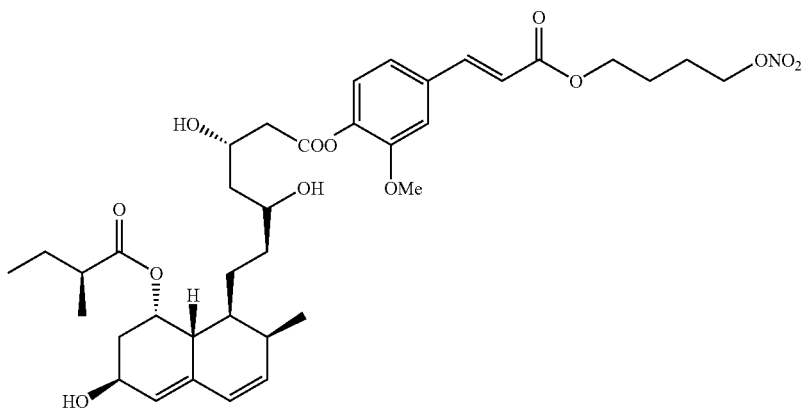

cerivastatin 4-(nitrooxy)butyl ester,
cerivastatin 4-(nitrooxymetyl)benzyl ester,
cerivastatin 3-(nitrooxymethyl)benzyl ester,
cerivastatin 2-(nitrooxymethyl)benzyl ester,
cerivastatin 4-(nitrooxymethyl)phenyl ester,
cerivastatin 3-(nitrooxymethyl)phenyl ester,
cerivastatin 2-(nitrooxymethyl)phenyl ester,
cerivastatin 2-[2'-(nitrooxy)ethyloxy]ethyl ester, corresponding to formula:

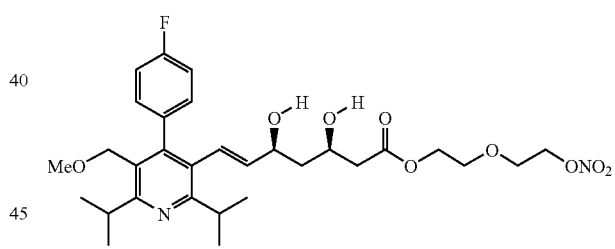

cerivastatin 2-methoxy-4-[[4'-(nitrooxy)butyl]trans-2-propenoyloxy]phenol ester, corresponding to formula:

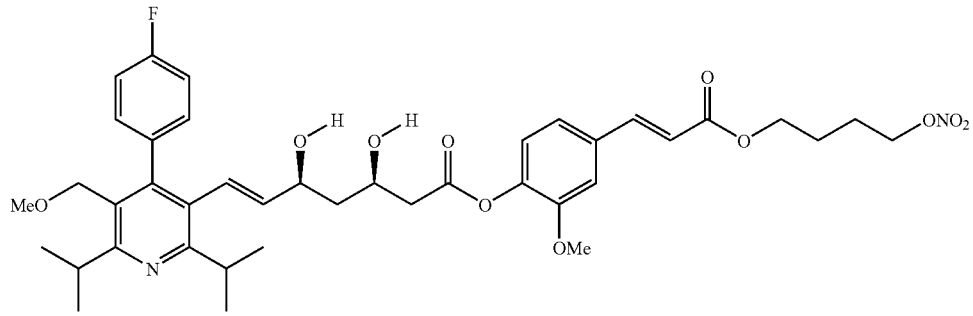

atorvastatin 4-(nitrooxy)butyl ester,
atorvastatin 4-(nitrooxymetyl)benzyl ester,
atorvastatin 3-(nitrooxymethyl)benzyl ester,
atorvastatin 2-(nitrooxymethyl)benzyl ester,
atorvastatin 4-(nitrooxymethyl)phenyl ester,
atorvastatin 3-(nitrooxymethyl)phenyl ester,
atorvastatin 2-(nitrooxymethyl)phenyl ester,
atorvastatin 2-[2'-(nitrooxy)ethyloxy]ethyl ester, corresponding to formula:

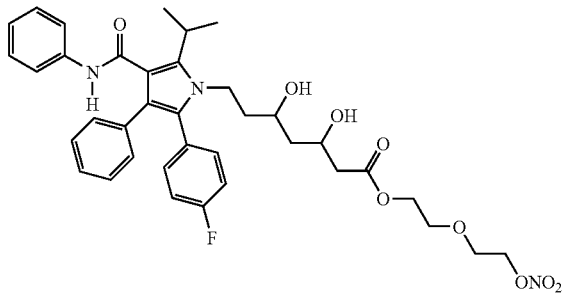

atorvastatin 2-methoxy-4-[[4'-(nitrooxy)butyl]trans-2-propenoyloxy]phenol ester, corresponding to formula:

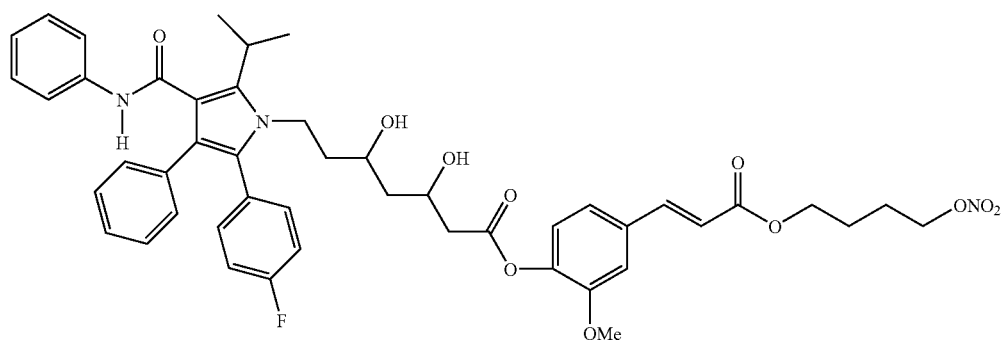

rosuvastatin 4-(nitrooxy)butyl ester,
rosuvastatin 4-(nitrooxymethyl)benzyl ester,
rosuvastatin 3-(nitrooxymethyl)benzyl ester,
rosuvastatin 2-(nitrooxymethyl)benzyl ester,
rosuvastatin 4-(nitrooxymethyl)phenyl ester,
rosuvastatin 3-(nitrooxymethyl)phenyl ester,
rosuvastatin 2-(nitrooxymethyl)phenyl ester,
rosuvastatin 2-[2'-(nitrooxy)ethyloxy]ethyl ester, corresponding to the formula:

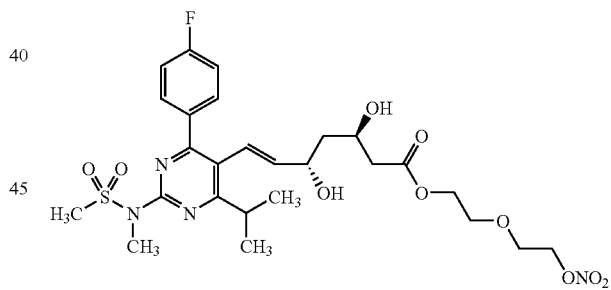

rosuvastatin 2-methoxy-4-[[4'-(nitrooxy)butyl]trans-2-propenoyloxy]phenol ester, corresponding to formula:

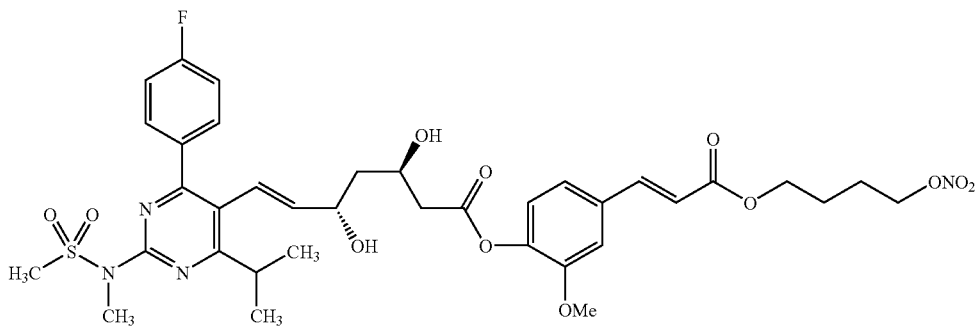

As mentioned above, object of the present invention are also pharmaceutical compositions containing at least a compound of the present invention of formula (I) together with non toxic adiuvants and/or carriers usually employed in the pharmaceutical field.

The daily dose of active ingredient that should be administered can be a single dose or it can be an effective amount divided into several smaller doses that are to be administered throughout the day. Usually, total daily dose may be in amounts preferably from 50 to 500 mg. The dosage regimen and administration frequency for treating the mentioned diseases with the compound of the invention and/or with the pharmaceutical compositions of the present invention will be selected in accordance with a variety of factors, including for example age, body weight, sex and medical condition of the patient as well as severity of the disease, route of administration, pharmacological considerations and eventual concomitant therapy with other drugs. In some instances, dosage levels below or above the aforesaid range and/or more frequent may be adequate, and this logically will be within the judgment of the physician and will depend on the disease state.

The compounds of the invention may be administered orally, parenterally, rectally or topically, by inhalation or aerosol, in formulations eventually containing conventional non-toxic pharmaceutically acceptable carriers, adjuvants and vehicles as desired. Topical administration may also involve the use of transdermal administration such as transdermal patches or iontophoresis devices. The term "parenteral" as used herein, includes subcutaneous injections, intravenous, intramuscular, intrasternal injection or infusion techniques.

Injectable preparations, for example sterile injectable aqueous or oleaginous suspensions may be formulated according to known art using suitable dispersing or wetting agents and suspending agents. The sterile injectable preparation may also be a sterile injectable solution or suspension in a non-toxic parenterally acceptable diluent or solvent. Among the acceptable vehicles and solvents are water, Ringer's solution and isotonic sodium chloride. In addition, sterile, fixed oils are conventionally employed as a solvent or suspending medium. For this purpose any bland fixed oil may be employed including synthetic mono or diglycerides, in addition fatty acids such as oleic acid find use in the preparation of injectables.

Suppositories for rectal administration of the drug can be prepared by mixing the active ingredient with a suitable non-irritating excipient, such as cocoa butter and polyethylene glycols.

Solid dosage forms for oral administration may include capsules, tablets, pills, powders, granules and gels. In such solid dosage forms, the active compound may be admixed with at least one inert diluent such as sucrose, lactose or starch. Such dosage forms may also comprise, as in normal practice, additional substances other than inert diluents, e.g. lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavouring and the like.

As previously reported, the new statin nitroderivatives beyond lowering lipid, possess enhanced anti-inflammatory, antiplatelet and antithrombotic effects as compared to native statins. Moreover, they can be effective also in the other pathologies such as acute coronary syndromes, stroke, peripheral vascular diseases such as peripheral ischemia, all disorders associated with endothelial dysfunctions such as vascular complications in diabetic patients and atherosclerosis, neurodegenerative diseases such as Alzheimer's disease (AD) and Parkinson's disease (PD), autoimmune diseases such as multiple sclerosis.

Study on Vascular Tone

The ability of statin nitroderivatives to induce vasorelaxation in comparison to native statins, was tested in vitro in isolated rabbit thoracic aorta preparations (Wanstall J. C. et al., Br. J. Pharmacol., 134:463–472, 2001). Male New Zealand rabbits were anaesthetized with thiopental-Na (50 mg/kg, iv), sacrificed by exsanguinations and then the thorax was opened and the aorta dissected. Single ring preparations (4 mm in length) of thoracic aorta were set up in physiological salt solution (PSS) at 37° C. in small organ chambers (5 ml). The composition of PSS was (mM): NaCl 130, $NaHCO_3$ 14.9, $KH_2PO_4$ 1.2, $MgSO_4$ 1.2, HEPES 10, $CaCl_2$, ascorbic acid 170 and glucose 1.1 (95% $O_2$/5% $CO_2$ pH 7.4). Each ring was mounted under 2 g passive tension in 5 ml organ bath. Isometric tension was recorded with a Grass transducer (Grass FT03) attached to a BIOPAC MP150 System. Preparations were allowed to equilibrate for 1 h, then contracted submaximally with noradrenaline (NA, 1 μM) and, when the contraction was stable, acetylcholine (ACh, 10 μM) was added. A relaxant response to ACh indicated the presence of a functional endothelium. When a stable precontraction was reached, a cumulative concentration-response curve to either of the vasorelaxant agents was obtained in the presence of a functional endothelium. Time intervals between different concentrations were based on the time needed to reach a full response. Moreover, the effect of the soluble guanylyl cyclase inhibitor ODQ (1-H-(1,2,4)-oxadiazol(4,3-a)quinoxalin-1-one) on the dilator responses elicited by the compounds was examined preincubating the aortic rings with ODQ (10 μM) for 20 min. Responses to vasorelaxing agents were measured from the plateau of NA contraction. The $IC_{50}$ (concentration giving 50% reversal of NA contraction) was interpolated from the plots of relaxant-response vs log molar concentration of tested compound.

During the experimental period, the plateau obtained with NA was stable without significant spontaneous loss of contraction in the aortic rings. Under these experimental conditions, native statins did not produce relaxation up to 30 μM, the curve being not different from that built up in presence of vehicle alone.

As shown in the following Table 1, the nitroderivatives of the invention were able to induce relaxation in a concentration-dependent manner. Furthermore, in experiments performed in presence of ODQ (10 μM), the vasorelaxant responses to all the tested drugs were inhibited.

TABLE 1

| Compound | $IC_{50}$ (μM) ± sem |
| --- | --- |
| Pravastatin | >30 |
| Compound of EX. 1 | 2.4 ± 0.6 |
| Fluvastatin | >30 |
| Compound of EX. 3 | 13.4 ± 3.5 |
| Compound of EX. 4 | 8.7 ± 3.3 |

$IC_{50}$ is the concentration which inhibits 50% of the response.

Effects of Nitrostatin Derivatives on Inflammatory Pathways In Vitro

The experiments were performed using RAW264.7 monocyte macrophage cell line. Cells were stimulated in the presence of LPS (1 μg/ml) for 8 h (pravastatin and derivative) or 16 h (fluvastatin, atorvastatin and derivatives). At the end of the incubation, the cells were harvested in lysis buffer and the protein content was measured. Western Blot of inducible iNOS and COX2 proteins (representatives of an ongoing inflammatory process) was performed. The obtained results reported in Table 2 are expressed as % reduction of optical density of each treatment vs. LPS-treated samples. Negative results indicate an increase vs. LPS alone.

TABLE 2

| Compound | Concentration (μM) | iNOS (% reduction vs LPS) | COX2 (% reduction vs LPS) |
| --- | --- | --- | --- |
| Fluvastatin | 10 | −14.8 ± 5.9 | −2.8 ± 3.7 |
| Compound of EX. 3 | 10 | 44.8 ± 11.9 | 53.9 ± 6.1 |
| Compound of EX. 4 | 10 | 22.4 ± 9.6 | 19.4 ± 6.5 |
| Pravastatin | 100 | 4.7 ± 3.6 | 26.9 ± 7.9 |
| Compound of EX. 1 | 100 | 55.2 ± 11.8 | 74.9 ± 4.4 |
| Atorvastatin | 10 | 20 ± 14 | — |
| Compound of EX. 7 | 10 | 45 ± 9 | — |

Nitroderivatives of fluvastatin, pravastatin and atorvastatin exert, in RAW264.7 cell line, a significant inhibitory action on the expression of proteins, such as COX2 and iNOS, that are recognised to be relevant in the inflammatory process. Conversely, these effects are not detectable or weak for the parent compounds.

Study of the Activity of Pravastatin Nitroderivative on Peripheral Vascular Disease Angiogenesis is a primary response to local tissue hypoxia and is likely involved in the restoration of blood flow in ischemic diseases such as acute coronary syndromes and occlusive peripheral vascular disease. The ability of pravastatin nitroderivative (compound of EX. 1) to inhibit the angiogenic process was evaluated using an in vivo model of murine hindlimb ischemia as previously described (Emanueli et al., Circulation 103,125–132, 2001). Briefly, 2 month-old CD1 male mice (Charles River, Italy) mice were randomly allocated into 3 groups (n=20 each) feed rat chow containing: 1) pravastatin (40 mg/kg), 2) pravastatin nitroderivative (48 mg/kg), 3) vehicle (regular chow). After 3 days, mice were anaesthetized and left hindlimb ischemia was induced by electro-coagulation of the upper part of femoral artery. Treatment was continued for the following 2 weeks after surgery. Systolic blood pressure was measured by tail cuff technique at 7 and 14 days. The clinical outcome at 14 days was determined by counting the number of necrotic or lost nails in the ischemic foot as well as the number of auto-amputation events. At 14 days from ischemia induction, hindlimbs of anaesthetized mice were perfusion-fixed, both adductors were coded and histologically processed. Capillary and arteriolar densities ($n_{cap}/mm^2$ and $n_{art}/mm^2$) were determined.

TABLE 3

| Compound | N capillaries/mm$^2$ in ischemic adductor muscle | N capillaries/mm$^2$ in contralateral adductor muscle |
| --- | --- | --- |
| Vehicle | 852 ± 32$^{§§}$ | 685 ± 38 |
| Pravastatin | 823 ± 42 | 736 ± 40 |
| Compound of EX. 1 | 1116 ± 53$^{§§**++}$ | 660 ± 40 |

**$P < 0.01$ vs. vehicle;
++$P < 0.01$ vs. pravastatin;
§§$P < 0.01$ vs. respective contralateral group As shown in Table 3, differently from the parent compound, the compound of the invention was able to potentiate the native reparative capillarization response to ischemia. The results of the present study indicate that the nitroderivative promotes a significant reparative neovascularization and ameliorates clinical outcome in mice with experimentally-induced hindlimb ischemia.

Effect of Pravastatin Nitroderivative on Leukocytes Adhesion in ApoE Knockout Mice The interaction between leukocytes and the vascular endothelium is a crucial inflammatory step in the atherogenic process. The ability of pravastatin nitroderivative (compound of EX. 1) to inhibit leukocyte adhesion was investigated ex vivo in atherosclerotic (ApoE knockout) mice.

Three groups of ApoE knockout mice were dosed with pravastatin (40 mg/kg po), pravastatin nitroderivative (equimolar dose) or vehicle daily for 5 days and euthanised by $CO_2$ euthanised by $CO_2$ asphyxiation 1 h after the last dose.

Leukocytes were isolated from spleen, centrifuged, RBCs lysed with water. Arterial segments prepared—aortic & thoracic regions opened longitudinally and pinned out luminal side up. Radiolabelled leukocytes ($^{51}$Cr-leukocytes) are incubated with thrombin-stimulated (10 UmL-1 for 10 min.) segments for 30 min. Segments are washed with medium and adhesion measured by gamma counter.

TABLE 4

| Compound | ApoE K/O mice Leukocyte adhesion (%) (thoracic aorta) |
|---|---|
| Vehicle | 23.4 ± 5 |
| Pravastatin | 23.0 ± 6 |
| Compound of EX. 1 | 9.3 ± 3*# |

*P < 0.05 vs vehicle;
P < 0.05 vs pravastatin

As shown in Table 4, differently from the parent compound, the compound of the invention was able to reduce the thrombin-induced adhesive interaction between isolated leukocytes and the blood vessel wall in both strains of mice.

These data demonstrate that the nitroderivative exerts anti-atherogenic/anti-inflammatory effects.

Study of Antithrombotic Activity of Pravastatin Nitroderivative In Vivo

The ability of pravastatin nitroderivative to inhibit thrombus formation was evaluated in male Charles Rivers CD-1 mice (20–25 g) given pravastatin (10 or 20 mg/kg ip), compound of EX. 1 (equimolar doses) or vehicle. 1–3 hrs later the animals were injected into a tail vein with U46619 (0.2 mg/kg), a stable TxA2 analog. As previously described (Momi et al., Eur. J. Pharmacol. 397:177–185, 2000), this dose of the agonist caused 80 to 90% mortality within 3 min. in the control group. In each experimental session at least six animals per treatment group were tested; control groups were run at the beginning and at the end of every experimental session. Protection against agonist-induced thromboembolism was expressed as $(1-T_{drug}/T_{saline}) \times 100$, were $T_{drug}$ is the mortality rate in drug-treated mice, and $T_{saline}$ is the number of non surviving control animals which received thrombin only.

The results were expressed as percentage of protection from U46619-induced pulmonary thromboembolism as compared to the control group.

TABLE 5

| Compound | Antithrombotic activity (%) 1-h before challenge | Antithrombotic activity (%) 3-h before challenge |
|---|---|---|
| Vehicle | 0 | 0 |
| Pravastatin | | |
| 10 mg/kg ip | 15 | 10 |
| 20 mg/kg ip | 25 | 20 |
| Compound of EX. 1 | | |
| 12 mg/kg ip | 30* | 40* |
| 24 mg/kg ip | 40*+ | 55*+ |

*P < 0.05 vs control;
+P < 0.05 vs pravastatin

As shown in Table 5, differently from the parent compound, the compound of the invention was able to inhibit thrombosis induced by U46619.

Study of Antiplatelet Activity of Pravastatin Nitroderivative In Vitro

Platelets are prominent components of the thrombi. The ability of prevastatin nitroderivative (compound of EX.1) to inhibit platelet aggregation was evaluated in vitro in human platelets. Platelet aggregation was measured in 0.25 ml platelet reached plasma (PRP) or gel filtered platelets (GEP) samples as previously described (Vezza R. eta!. Blood 82: 2704–2713. 1993).

Compounds were incubated at 37° C. for 2 min before adding U46619, an aggregating agent, $TxA_2$ analog. Aggregation was followed for 5 min and the maximal amplitude (cm) was measured. DMSO (0.05%) was used as vehicle. Compounds were tested at concentrations ranging from 50 to 200 µM.

TABLE 6

| Compound | Platelet aggregation (GFP) $IC_{50}$ µM | Platelet aggregation (PRP) $IC_{50}$ µM |
|---|---|---|
| Pravastatin | >200 | >200 |
| Compound of EX. 1 | 101 ± 10 | 74 ± 7 |

As shown in Table 6, differently from the parent compound, the nitroderivative of the invention was able to inhibit platelet aggregation induced by U46619.

Effect of Pravastatin Nitroderivative on Inhibition of Tissue Factor Expression In Vitro Tissue factor (TF) is a major regulator of homeostasis and thrombosis. The ability of pravastatin nitroderivative (compound of EX. 1) to inhibit TF expression was evaluated in isolated human blood mononuclear cell (MNC) preparations. MNC were obtained from fresh blood by density gradient (Ficoll-Hypaque) centrifugation and resuspended in serum-free RPMI medium at the concentration of $2-3 \times 10^6$/ml. Pravastatin nitroderivative (3–50 µM) or pravastatin (50 µM) was added to cell suspensions prior to exposure to LPS (1 µg/ml). After incubation for 3 h at 37° C., TF expression in MNC was assessed by 1) functional assay (Semeraro et al., 1983. Immunology; 50: 529–35) on intact cells; 2) immunological assay (Imubind, Instrumentation Laboratory, Milan) on Triton X-100 cell extracts; 3) RT-PCR (Rossiello et al. Thromb Haemost 2000; 84:453–59).

TABLE 7

| | TF in LPS-stimulated MNC | |
|---|---|---|
| Compound | Activity (AU/10⁶ cells)§ | Antigen (ng/mg protein) |
| Vehicle (DMSO 0.1%) | 178 ± 36.2 | 5.0 ± 1.1 |
| Pravastatin (50 µM) | 189 ± 37.6 | 4.4 ± 1.3 |
| Compound of EX. 1 (50 µM) | 16 ± 4.9** | 0.65 ± 0.11** |

Data are the mean ± SEM of 4–5 experiments.
§Arbitrary units calculated by reference to a standard curve constructed with human relipidated tissue factor
**P < 0.01 vs pravastatin and vehicle As shown in Table 7, differently from the parent compound, the compound of the invention markedly inhibited LPS-induced TF expression (activity and antigen).

The results of the present study indicate that the nitroderivative exerts antithrombotic activity.

The following examples are to further illustrate the invention without limiting it.

General Procedure

The compound of general formula (I), wherein X=O, can be obtained by reacting a compound of formula (II)

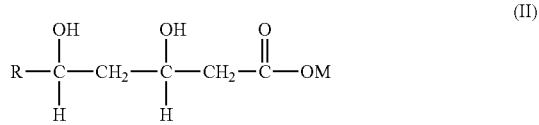

(II)

wherein M is hydrogen or an alkali metal or alkaline earth metal, such as sodium or calcium, with a compound of formula (III)

(III)

wherein A is a leaving group such as chlorine, bromine, iodine, a tosyl or mesyl group, B is selected from chlorine, bromine, iodine or a nitrooxy group and Y is as defined above in formula (I), in an inert organic solvent such as N,N'-dimethylformamide, tetrahydrofurane, benzene, toluene, at a temperature ranging from room temperature to 50° C. The reaction is terminated within 30 min to 24 h.

The compounds of formula (II) are known compounds available on the market or can be prepared according to methods well known in the literature. The compounds of formula (III), wherein A is as above defined and B is Cl, Br, I, are commercially available or can be synthesized according to methods well known in the literature.

The compounds of formula (III), wherein A is as above defined and B is $ONO_2$, are synthesized by conversion of a compound of formula (III) wherein B is Cl, Br, I into the corresponding nitro derivative by reaction with a nitrate source such as silver nitrate, lithium nitrate, sodium nitrate, potassium nitrate, magnesium nitrate, calcium nitrate, iron nitrate, zinc nitrate or tetraalkylammonium nitrate (wherein alkyl is $C_1$–$C_{10}$ alkyl) in a suitable organic solvent such as acetonitrile, tetrahydrofurane, methyl ethyl ketone, ethyl acetate, DMF, the reaction is carried out, in the dark, at a temperature from room temperature to the boiling temperature of the solvent. The reaction is terminated within 30 min to 3 days. Preferred nitrate source is silver nitrate.

The compound of formula (I), in which X=O, S, NH or $NR^1$, $R^1$ being as above defined, can be obtained by reacting a compound of formula (II) wherein M is hydrogen, in presence of a dehydrating agent, with a compound of formula (IV)

(IV)

wherein Y e B are as defined above and D is selected from $NH_2$, $NHR^1$, OH or SH, $R^1$ being as above defined. Preferred dehydrating agents are N,N'-carbonyldiimidazole, used in presence of a catalytic amount of sodium ethylate, DCC EDAC. The reaction is performed in an inert organic solvent such as N,N'-dimethylformamide, tetrahydrofurane, benzene, toluene, a polyhalogenated aliphatic hydrocarbon, at a temperature ranging from −50° C. to 50° C. for between 30 min and 24 h.

The compounds of formula (IV), wherein D is as above defined and B is Cl, Br, I, are commercially available or synthesized according to methods well known in the literature.

For example they can be obtained from the corresponding hydroxy derivative of formula (V) D-Y—OH, by reaction with thionyl or oxalyl chloride, halides of $P^{III}$ or $P^V$, mesyl chloride, tosyl chloride in solvents inert such as toluene, chloroform, DMF, etc.

The compounds of formula (IV), wherein D is as above defined and B is $ONO_2$, can be obtained by reaction of the compounds of formula (IV) wherein B is Cl, Br, I, with a nitrate source as above described. Alternatively the compounds of formula (IV) wherein B is $ONO_2$, can be obtained by the corresponding hydroxy compounds of formula (V) by reaction with nitric acid and acetic anhydride in a temperature range from −50° C. to 0° C. according to methods well known in the literature.

EXAMPLE 1

Synthesis of [1S-[1α(βS*,δS*),2α,6α,8β-(R*), 8aα]]-1,2,6,7,8,8a-hexahydro-β,δ,6-trihydroxy-2-methyl-8-(2-methyl-1-oxobutoxy)-1-naphthaleneheptanoic acid 4-(nitrooxy)butyl ester (Pravastatin 4-(nitrooxy)butyl ester)

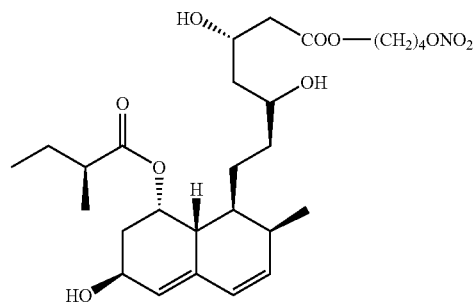

a) [1S-[1α(βS*,δS*),2α,6α,8β-(R*),8aα]]-1,2,6,7,8,8a-hexahydro-β,δ,6-trihydroxy-2-methyl-8-(2-methyl-1-oxobutoxy)-1-naphthaleneheptanoic Acid 4-bromobutyl ester To a solution of pravastatin sodium (9.25 g, 21 mmol) in N,N-dimethylformamide (70 ml) a mixture of 1,4-dibromobutane (3.68 ml, 31 mmol) in N,N-dimethylformamide (30 ml) was added dropwise. The reaction mixture was stirred at room temperature for 24 h. The solution was then treated with water and diethyl ether, the organic layers were dried with sodium sulfate and concentrated under reduced pressure. The residue was purified by flash chromatography, with n-hexane/ethyl acetate 3/7 as eluent. The title compound was obtained as a white powder (7.8 g).

b) [1S-[1α(βS*,δS*),2α,6α,8β-(R*),8aα]]-1,2,6,7,8,8a-hexahydro-β,δ,6-trihydroxy-2-methyl-8-(2-methyl-1-oxobutoxy)-1-naphthaleneheptanoic Acid 4-(nitrooxy)-butyl ester A solution of the compound obtained as described in a) above (7.7 g, 14 mmol) and silver nitrate (3.5 g, 21 mmol) in acetonitrile (90 ml) was stirred at 40° C., in the dark, for 48 h. The precipitate thus formed (silver salt) was filtered off and the solvent was evaporated under vacuum. The residue was then purified by flash chromatography, with n-hexane/ethyl acetate 3/7 as eluent. The title compound was obtained as a white powder (3.7 g) melting at 63° C.

¹H-NMR: δ(CDCl₃) 6.00(1H, m); 5.88(1H, m); 5.53(1H, s); 5.40(1H, s); 4.51(2H, t); 4.40(1H, m); 4.26(1H, m); 4.15(2H, t); 3.78(1H, m); 2.60–2.23(6H, m); 1.8–1.20(14H, m); 1.10(3H, d); 0.87(6H, t).

EXAMPLE 2

Synthesis of [1S-[1α(βS*,δS*),2α,6α,8β-(R*),8aα]]-1,2,6,7,8,8a-hexahydro-β,δ,6-trihydroxy-2-methyl-8-(2-methyl-1-oxobutoxy)-1-naphthalene-heptanoic acid 4-(nitrooxymethyl)benzyl ester (Pravastatin 4-(nitro-oxymethyl)benzyl ester)

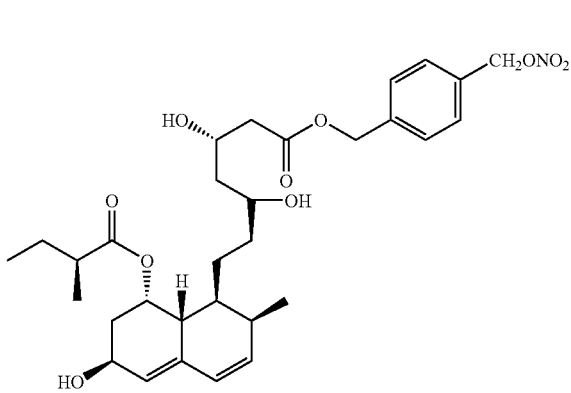

a) 1S-[1α(βS*,δS*), 2α,6α,8β-(R*),8aα]]-1,2,6,7,8,8a-Hexahydro-β,δ,6-trihydroxy-2-methyl-8-(2-methyl-1-oxobutoxy)-1-naphthaleneheptanoic acid 4-(chloro-methyl)benzyl ester To a solution of α,α'-dichloro-p-xylene (5.5 g, 31 mmol) in N,N-dimethylformamide (70 ml) pravastatin sodium (7 g, 15 mmol) was added portionwise. The reaction mixture was stirred at room temperature for 24 h. The solution thus obtained was then treated with water and ethyl acetate, the organic layers were anidrified with sodium sulfate and concentrated under reduced pressure. The residue was purified by silica gel chromatography, with n-hexane/ethyl acetate 1/1 as eluent. The title compound was obtained as a white powder (5.5 g) and was employed as such in the following step without further purification.

b) [1S-[1α(βS*,δS*),2α,6α,8β-(R*),8aα]]-1,2,6,7,8,8a-Hexahydro-β,δ,6-trihydroxy-2-methyl-8-(2-methyl-1-oxobutoxy)-1-naphthaleneheptanoic acid 4-(nitrooxymethyl) benzyl ester A solution of the compound obtained as described in a) above (5.5 g, 7.7 mmol) and silver nitrate (2.5 g, 15 mmol) in acetonitrile (60 ml) was stirred at 60° C., in the dark, for 48 h. The precipitate thus formed (silver salt) was filtered off and the solvent was evaporated under vacuum. The residue was then purified by flash chromatography, with n-hexane/ethyl acetate 1/1 as eluent. The title compound (1.6 g) was obtained as white powder melting at 80–82° C.

¹H-NMR δ(CDCl₃):7.39(4H, m); 5.98(1H, m); 5.86(1H, m); 5.54(1H, s); 5.42(3H, s); 5.16(2H, s); 4.40(1H, m); 4.27(1H, m); 3.80(1H, m); 2.52(3H, m); 2.45–2.25(3H, m); 1.74–1.10(10H, m) 1.10(3H, d); 0.87(6H, t).

EXAMPLE 3

Synthesis of [R*,S*-(E)]-7-[3-(4-fluorophenyl)-1-(1-methylethyl)-1H-indol-2-yl]-3,5-dihydroxy-6-heptanoic acid 4-(nitrooxy)butyl ester (fluvastatin 4-(nitrooxy)butyl ester)

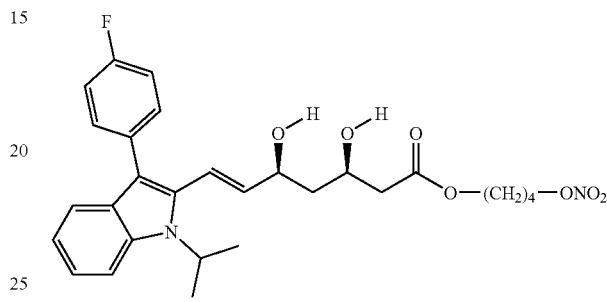

a) [R*,S*-(E)]-7-[3-(4-fluorophenyl)-1-(1-methylethyl)-1H-indol-2-yl]-3,5-dihydroxy-6-heptanoic acid 4-bromobutyl ester To a solution of 1,4-dibromobutane (4.1 ml, 34 mmol) in N,N-dimethylformamide (60 ml) a mixture of fluvastatin sodium (5 g, 11 mmol) in N,N-dimethylformamide (40 ml) was added dropwise. The reaction mixture was stirred at room temperature for 24 h. The resulting solution was then treated with water and diethyl ether, the organic layers were anidrified with sodium sulfate and concentrated under reduced pressure. The residue was purified by flash chromatography, with n-hexane/iso-propanol 8.5/1.5 as eluent. The title compound was obtained as yellow oil (4.7 g) and was employed in the following step without further purification.

b) [R*,S*-(E)]-7-[3-(4-fluorophenyl)-1-(1-methylethyl)-1H-indol-2-yl]-3,5-dihydroxy-6-heptanoic acid 4-(nitrooxy)butyl ester A solution of the compound obtained as described in a) above (4.7 g, 8.5 mmol) and silver nitrate (2.9 g, 17 mmol) in acetonitrile (60 ml) was stirred at 60° C., in the dark, for 48 h. The precipitate thus formed (silver salt) was filtered off and the solvent was evaporated under vacuum. The residue was then purified by flash chromatography, with n-hexane/ethyl acetate 1/1 as eluent. The desired product (0.5 g) was obtained as white powder melting at 112° C.

¹H-NMR δ(DMSO): 7.69(1H, d); 7.43(3H, m); 7.27(2H, t); 7.25(1H, t); 7.03(1H, t); 6.65(1H, d); 5.75(1H, dd); 4.98(1H, d); 4.90(1H, m); 4.78(1H, d); 4.50(2H, t); 4.25(1H, m); 4.09(2H, t); 3.9(1H, m); 2.4(2H, m); 1.67(4H, m); 1.61(6H, d); 1.42(2H, m).

EXAMPLE 4

Synthesis of [R*,S*-(E)]-7-[3-(4-fluorophenyl)-1-(1-methylethyl)-1H-indol-2-yl]-3,5-dihydroxy-6-heptanoic acid 4-(nitrooxymethyl)benzyl ester (fluvastatin 4-(nitrooxymethyl)benzyl ester)

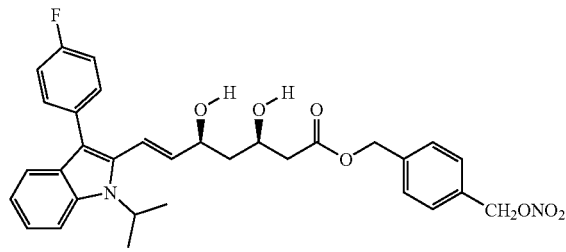

a) [R*,S*-(E)]-7-[3-(4-fluorophenyl)-1-(1-methylethyl)-1H-indol-2-yl]-3,5-dihydroxy-6-heptanoic acid 4-(chloromethyl)benzyl ester To a solution of α,α'-dichloro-p-xylene (10 g, 57 mmol) in N,N-dimethylformamide (60 ml) a mixture of fluvastatin sodium (10 g, 23 mmol) in N,N-dimethylformamide (80 ml) was added dropwise. The reaction mixture was stirred in the dark at room temperature for 12 h. The solution was then treated with water and ethyl acetate, the organic layers were anidrified with sodium sulfate and concentrated under reduced pressure. The residue was purified by flash chromatography, with n-hexane/ethyl acetate 1/1 as eluent. The title compound (9.4 g) was obtained as white powder by crystallization from n-hexane.

b) [R*,S*-(E)]-7-[3-(4-fluorophenyl)-1-(1-methylethyl)-1H-indol-2-yl]-3,5-dihydroxy-6-heptanoic acid 4-(nitrooxymethyl)benzyl ester A solution of the compound described in a) above (9.4 g, 17 mmol) and silver nitrate (10.6 g, 63 mmol) in acetonitrile (180 ml) was stirred at 50° C., in the dark, for 24 h. The precipitate thus obtained (silver salt) was filtered off and the solvent was evaporated under vacuum. The residue was then purified by flash chromatography, with n-hexane/ethyl acetate 4/6 as eluent to give the desired product (4 g) as a white powder melting at 103–104° C.

$^1$H-NMR δ(DMSO): 7.65(1H, d); 7.42(7H, m); 7.22(2H, t); 7.15(1H, t); 7.03(1H, t); 6.64(1H, d); 5.75(1H, dd); 5.51(2H, s); 5.12(2H, s); 4.98(1H, d); 4.88(1H, t); 4.84(1H, d); 4.27(1H, t); 3.94(1H, t); 2.4–2.6(2H, m); 1.4–1.7(2H,M); 1.57(6H, d).

EXAMPLE 5

Synthesis of [R*,S*-(E)]-7-[3-(4-fluorophenyl)-1-(1-methylethyl)-1H-indol-2-yl]-3,5-dihydroxy-6-heptanoic acid 3-(nitrooxymethyl)benzyl ester (fluvastatin 3-(nitrooxymethyl)benzyl Ester)

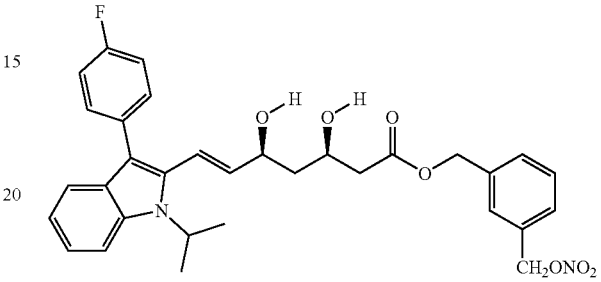

a) [R*,S*-(E)]-7-[3-(4-fluorophenyl)-1-(1-methylethyl)-1H-indol-2-yl]-3,5-dihydroxy-6-heptanoic acid 3-(chloromethyl)benzyl ester To a solution of α,α'-dichloro-m-xylene (0.95 g, 5.4 mmol) in N,N-dimethylformamide (25 ml) a mixture of fluvastatin sodium (0.79 g, 1.8 mmol) in N,N-dimethylformamide (25 ml) was added dropwise. The reaction mixture was stirred in the dark at room temperature for 24 h. The solution thus formed was then treated with water and ethyl acetate, the organic layers were anidrified with sodium sulfate and concentrated under reduced pressure. The residue was purified by silica gel chromatography, with n-hexane/ethyl acetate 1/1 as eluent, to give 0.41 g of the title compound.

b) [R*,S*-(E)]-7-[3-(4-fluorophenyl)-1-(1-methylethyl)-1H-indol-2-yl]-3,5-dihydroxy-6-heptanoic acid 3-(nitrooxymethyl)benzyl ester A solution of the compound described above (0.4 g, 0.7 mmol) and silver nitrate (0.36 g, 2.1 mmol) in acetonitrile (30 ml) was stirred at 45° C., in the dark, for 24 h. The precipitate thus obtained (silver salt) was filtered off and the solvent was evaporated under vacuum. The residue was purified by flash chromatography, with methylene chloride/iso-propanol 9.5/0.5 as eluent to give the desired product (0.2 g).

$^1$H-NMR: δ(DMSO): 7.67(1H, d); 7.47–7.40(7H, m); 7.25-7.10(3H, m); 7.05(1H, t); 6.62(1H, d); 5.72(1H, dd); 5.49(2H, s); 5.13(2H, s); 5.00–4.84(3H, m); 4.27(1H, m); 3.95(1H, m); 2.60–2.35(2H, m); 1.58(6H, d); 1.70–1.45(2H, m).

EXAMPLE 6

Synthesis of [R*,S*-(E)]-7-[3-(4-fluorophenyl)-1-(1-methylethyl)-1H-indol-2-yl]-3,5-dihydroxy-6-heptanoic acid 2-(nitrooxymethyl)benzyl ester (fluvastatin 2-(nitrooxymethyl)benzyl ester)

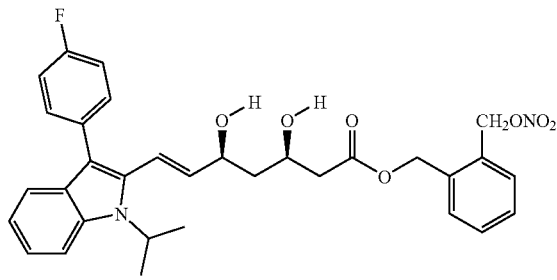

a) [R*,S*-(E)]-7-[3-(4-fluorophenyl)-1-(1-methyl-ethyl)-1H-indol-2-yl]-3,5-dihydroxy-6-heptanoic acid 2-(chloromethyl)benzyl ester To a solution of α,α'-dichloro-o-xylene (1.5 g, 3.4 mmol) in N,N-dimethylformamide (15 ml) a mixture of fluvastatin sodium (1.5 g, 8.6 mmol) in N,N-dimethylformamide (15 ml) was added dropwise. The reaction mixture was stirred in the dark at room temperature for 24 h. The solution thus obtained was treated with water and ethyl acetate, the organic layers were anidrified with sodium sulfate and concentrated under reduced pressure. The residue was purified by silica gel chromatography, with n-hexane/ethyl acetate 6/4 as eluent to give 0.97 g of the title compound.

b) [R*,S*-(E)]-7-[3-(4-fluorophenyl)-1-(1-methyl-ethyl)-1H-indol-2-yl]-3,5-dihydroxy-6-heptanoic acid 2-(nitrooxymethyl)benzyl ester A solution of the compound obtained as described above (0.97 g, 1.7 mmol) and silver nitrate (1.3 g, 7.6 mmol) in acetonitrile (40 ml) was stirred at 40° C., in the dark, for 24 h. The precipitate thus formed (silver salt) was filtered off and the solvent was evaporated under vacuum. The residue was then purified by flash chromatography, with n-hexane/iso-propanol 8.5/1.5 as eluent to give the desired product (0.42 g) as yellow powder.

$^1$H-NMR δ(DMSO): 6.52 (1H, m); 7.47–7.30 (7H, m); 7.24-7.14(3H, m); 7.03(1H, t); 6.27(1H, d); 5.70(1H, dd); 5.66(2H, s); 5.22(2H, s); 4.98(1H, m); 4.84(1H, t); 4.82(1H, d); 4.30(1H, m); 3.90(1H, m); 2.40(2H, m); 1.58(6H, d); 1.40(2H, m).

EXAMPLE 7

Synthesis of (βR,δR)-2(4-fluorophenyl)-β,δ-dihydroxy-5-(1-methylethyl)-3-phenyl-4-[(phenylamino)carbon-yl]-1H-pyrrole-1-heptanoic acid 4-(nitrooxy)butyl ester (atorvastatin 4-(nitrooxy)butyl ester)

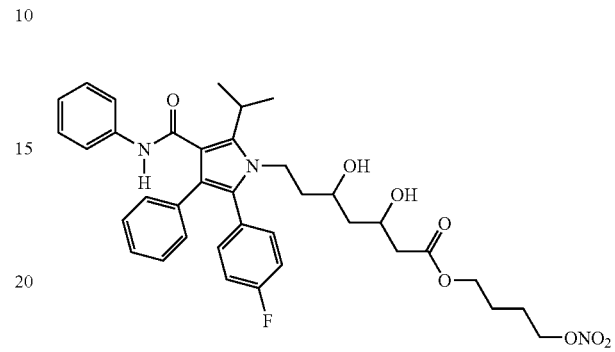

a) (βR,δR)-2(4-fluorophenyl)-β,δ-dihydroxy-5-(1-methylethyl)-3-phenyl-4-[(phenylamino)carbonyl]-1H-pyrrole-1-heptanoic acid 4-bromobutyl ester To a solution of 1,4-dibromobutane (0.34 ml, 2.88 mmol) in N,N-dimethylformamide (10 ml) a mixture of atorvastatin calcium (0.83 g, 0.72 mmol) in N,N-dimethylformamide (10 ml) was added dropwise. The reaction mixture was stirred at room temperature for 24 h. The solution was then treated with water and diethyl ether, the organic layers were anidrified with sodium sulfate and concentrated under reduced pressure. The residue was purified by silica gel chromatography, with n-hexane/ethyl acetate 6/4 as eluent to give the title compound (0.26 g) as a white solid.

b) (βR,δR)-2(4-fluorophenyl)-β,δ-dihydroxy-5-(1-methylethyl)-3-phenyl-4-[(phenylamino)carbonyl]-1H-pyrrole-1-heptanoic acid 4-(nitrooxy)butyl ester A solution of the compound obtained in a) above (0.25 g, 0.36 mmol) and silver nitrate (0.38 g, 2.2 mmol) in acetonitrile (10 ml) was stirred at 50° C., in the dark, for 21 h. The precipitate thus formed (silver salt) was filtered off and the solvent was evaporated under vacuum. The residue was then purified by silica gel chromatography, with n-hexane/ethyl acetate 1/1 as eluent to give the desired product (0.21 g) was as white powder.

$^1$H-NMR δ(DMSO): 9.80 (1H, s); 7.51 (2H, d); 7.26–7.19 (6H, m); 7.09–6.95 (6H, m); 4.73 (1H, d); 4.61 (1H, d); 4.54 (2H, t); 4.04 (2H, t); 4.00–3.70 (3H, m); 3.50 (1H, m); 3.22(1H, m); 2.40 (1H, dd); 2.25 (1H, dd); 1.80–1.10 (8H, m); 1.38 (6H, d).

According to Examples 1–7 further compounds of the invention can be obtained starting from appropriate reactants and employing also cerivastatin and rosuvastatin instead of pravastatin, fluvastatin and atorvastatin.

The invention claimed is:

1. A compound of general formula (I) or a pharmaceutically acceptable salt or stereoisomer thereof

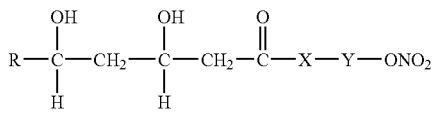
(I)

wherein:
X is —O—, —S—, —NH— or —NHR$^1$—, R$^1$ being straight or branched alkyl with 1 to 10 carbon atoms;
R is a statin residue of formula

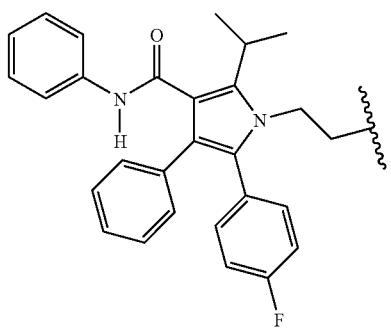

Y is a bivalent radical having the following meaning:
a)
straight or branched C$_1$–C$_{20}$ alkylene being optionally substituted with one or more of the substituents selected from the group consisting of: halogen atoms, hydroxy, —ONO$_2$ or T$_0$, wherein T$_0$ is —OC(O)(C$_1$–C$_{10}$ alkyl)—ONO$_2$ or —O(C$_1$–C$_{10}$ alkyl)—ONO$_2$;
cycloalkylene with 5 to 7 carbon atoms in the cycloalkylene ring, the ring being optionally substituted with side chains T, wherein T is straight or branched alkyl with from 1 to 10 carbon atoms;

b)
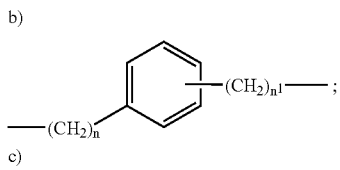

c)
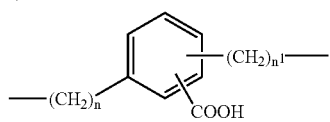

wherein n is an integer from 0 to 20, and n$^1$ is an integer from 1 to 20;

d)
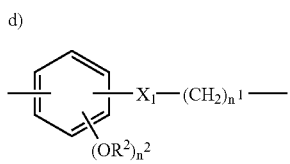

wherein:
n$^1$ is as defined above and n$^2$ is an integer from 0 to 2;
X$_1$=—OCO— or —COO—and R$^2$ is H or CH$_3$;

e)
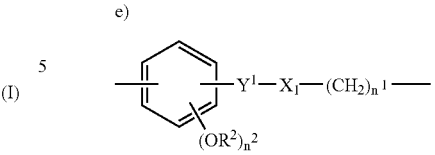

wherein:
n$^1$, n$^2$, R$^2$ and X$_1$ are as defined above;
Y$^1$ is —CH$_2$—CH$_2$— or —CH=CH—(CH$_2$)$_{n^2}$—;

f)
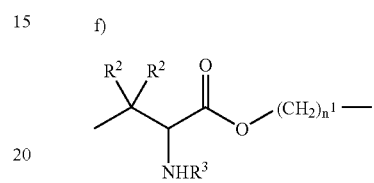

wherein:
n$^1$ and R$^2$ are as defined above, R$^3$ is H or COCH$_3$;
with the proviso that when Y is selected from bivalent radicals mentioned under b)-f), the —ONO$_2$ group is bound to —(CH$_2$)$_{n^1}$;

g)
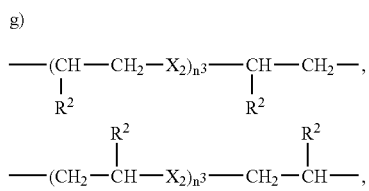

wherein X$_2$ is —O— or —S—, n$^3$ is an integer from 1 to 6, R$^2$ is as defined above;

h)
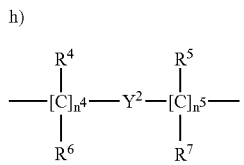

wherein:
n$^4$ is an integer from 0 to 10;
n$^5$ is an integer from 1 to 10;
R$^4$, R$^5$, R$^6$, R$^7$ are the same or different, and are H or straight or branched C$_1$–C$_4$-alkyl;
wherein the —ONO$_2$ group is bound to

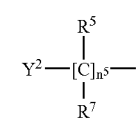

n$^5$ being as defined above;
Y$^2$ is a 5 or 6 member saturated, unsaturated or aromatic heterocyclic ring, containing one or more heteroatoms selected from nitrogen, oxygen, or sulfur.

2. A compound of general formula (I) and/or a pharmaceutically acceptable salt or stereoisomer thereof according to claim 1 wherein:

X is —O— or —S—;
R is a statin residue as defined in claim 1;
Y is a bivalent radical having the following meaning:

a) straight or branched $C_1$–$C_{10}$ alkylene, being optionally substituted with $T_0$, wherein $T_0$ is as defined in claim 1;

b) 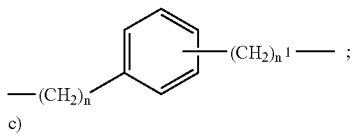

c) 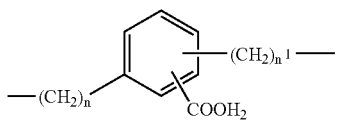

wherein n is an integer from 0 to 5, and $n^1$ is an integer from 1 to 5;

d) 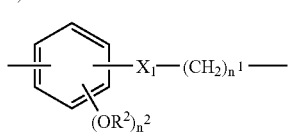

wherein:
$n^1$ is as defined above and n is an integer from 0 to 2;
$X_1$=—OCO— or —COO— and $R^2$ is H or $OH_3$;

e) 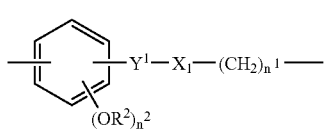

wherein:
$n^1$, $n^2$, $R^2$ and $X_1$ are as defined above;
$Y^1$ is —CH=CH—;

f) 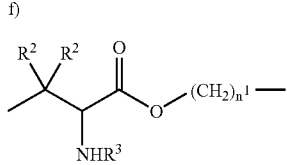

wherein:
$n^1$ and $R^2$ are as defined above, $R^3$ is H or $COCH_3$;
with the proviso that when Y is selected from the bivalent radicals mentioned under b)-f), the —$ONO_2$ group is bound to —$(CH_2)_{n^1}$;

g) 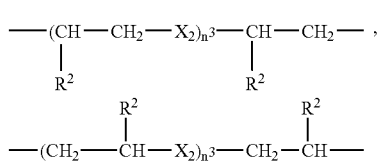

wherein $X_2$ is —O— or —S—, $n^3$ is an integer from 1 to 4, $R^2$ is as defined above;

h) 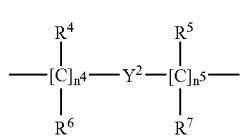

wherein:
$n^4$ is an integer from 0 to 3;
$n^5$ is an integer from 1 to 3;
$R^4$, $R^5$, $R^6$, $R^7$ are the same and are H;
and wherein the —$ONO_2$ group is linked to

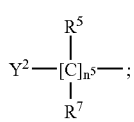

$Y^2$ is a 6 member saturated, unsaturated or aromatic heterocyclic ring, containing one or more atoms of nitrogen.

3. A compound of formula (I) according to claim 1, that is atorvastatin 4-(nitrooxy)butyl ester.

4. A compound of formula (I) according to claim 1, that is atorvastatin 4-(nitrooxymethyl)-benzyl ester.

5. A compound of formula (I) according to claim 1, that is atorvastatin 3-(nitrooxymethyl)-benzyl ester.

6. A compound of formula (I) according to claim 1, that is atorvastatin 2-(nitrooxymethyl)-benzyl ester.

7. A compound of formula (I) according to claim 1, that is atorvastatin 4-(nitrooxymethyl)-phenyl ester.

8. A compound of formula (I) according to claim 1, that is atorvastatin 3-(nitrooxymethyl)-phenyl ester.

9. A compound of formula (I) according to claim 1, that is atorvastatin 2-(nitrooxymethyl)-phenyl ester.

10. A compound of formula (I) according to claim 1, that is atorvastatin 2-[2'-(nitrooxy)ethyloxy]ethyl ester.

11. A compound of formula (I) according to claim 1, that is atorvastatin 2-methoxy-4-[[4'-nitrooxy)butyl[trans-2-propenoyloxy]phenol ester.

12. A method of reducing inflammatory, thrombotic and platelet activity, comprising administering to a patient in need thereof an effective amount of a compound according to claim 1.

13. A method of reducing cholesterol and triglycerides levels and/or for raising high density lipoprotein cholesterol ("HLP-C") levels, comprising administering an effective amount of a compound according to claim 1.

14. A method of treating acute coronary syndromes, stroke, peripheral vascular diseases, vascular complications in diabetic patients and atherosclerosis comprising administering an effective amount of a compound according to claim 1.

15. The method according to claim 14, wherein the peripheral vascular disease is peripheral ischemia.

16. A pharmaceutical composition comprising a pharmaceutically acceptable carrier and a pharmaceutically effective amount of a compound of general formula (I) and/or a salt or stereoisomer thereof according to claim 1.

17. A pharmaceutical composition according to claim 16 in a suitable form for the oral, parenteral, rectal, topic and transdermic administration, by inhalation spray or aerosol or iontophoresis devices.

18. Liquid or solid pharmaceutical composition for oral, parenteral, rectal, topic and transdermic administration or inhalation in form of tablets, capsules and pills eventually with enteric coating, powders, granules, gels, emulsions solutions, suspensions, syrups, elixir, injectable forms, suppositories, in transdermal patches or liposomes, containing a compound of formula (I) according to claim 1 and/or a salt or stereoisomer thereof and a pharmaceutically acceptable carrier.

19. A pharmaceutical composition comprising a compound of formula (I), according to claim 1 at least a compound used to treat cardiovascular disease and a pharmaceutically acceptable carrier.

20. A pharmaceutical composition according to claim 19, wherein the compound used to treat cardiovascular disease is selected from the group consisting of: ACE inhibitors, angiotensin II receptor antagonists, beta-adrenergic blockers, calcium channel blockers, antithrombotics, aspirin, nitrosated ACE inhibitors, nitrosated angiotensin II receptor antagonists, nitrosated beta-adrenergic blockers and nitrosated aspirin.

21. A pharmaceutical kit comprising the composition of claim 16 and a compound used to treat cardiovascular disease.

* * * * *